United States Patent
Tvsk et al.

(10) Patent No.: US 11,613,540 B2
(45) Date of Patent: Mar. 28, 2023

(54) SOLID STATE FORMS OF VENETOCLAX AND ITS PROCESS FOR THE PREPARATION THERE OF

(71) Applicant: Alembic Pharmaceuticals Limited, Vadodara (IN)

(72) Inventors: Vittal Tvsk, Vadodara (IN); Dinesh Chudasama, Vadodara (IN); Saisuryanarayana Donthukurthi, Vadodara (IN); Tejas Shah, Vadodara (IN); Chetan Patil, Vadodar (IN); Mahendar Velisoju, Vadodara (IN); Mahender Rao Siripragada, Vadodara (IN)

(73) Assignee: Alembic Pharmaceuticals Limited, Vadodara (IN)

( * ) Notice: Subject to any disclaimer, the term of this patent is extended or adjusted under 35 U.S.C. 154(b) by 99 days.

(21) Appl. No.: 17/141,541

(22) Filed: Jan. 5, 2021

(65) Prior Publication Data
US 2021/0130350 A1 May 6, 2021

Related U.S. Application Data

(63) Continuation of application No. 16/965,672, filed as application No. PCT/IB2019/050706 on Jan. 29, 2019, now Pat. No. 10,934,289.

(30) Foreign Application Priority Data

Jan. 30, 2018 (IN) .............................. 201821003505

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
None
See application file for complete search history.

(56) References Cited

U.S. PATENT DOCUMENTS 10,934,289 B2 * 3/2021 Tvsk .................... C07D 471/04

FOREIGN PATENT DOCUMENTS

| EP | 3412666 A1 | 12/2018 |
|---|---|---|
| WO | 2017212431 A1 | 12/2017 |

OTHER PUBLICATIONS

PCT International Search Report and Written Opinion in PCT/IB2019/050706 dated Apr. 18, 2019, 14 pages.

* cited by examiner

*Primary Examiner* — Brian J Davis
(74) *Attorney, Agent, or Firm* — Sterne, Kessler, Goldstein & Fox P.L.L.C.

(57) ABSTRACT

The present invention provides solid state forms of Venetoclax, particularly relates to novel alkali metal salt and/or DMF solvate form of Venetoclax or its salt. The present invention also relates to process for the preparation Venetoclax by using the said solid state form of Venetoclax.

18 Claims, 4 Drawing Sheets

SOLID STATE FORMS OF VENETOCLAX AND ITS PROCESS FOR THE PREPARATION THERE OF

CROSS-REFERENCE TO RELATED APPLICATIONS

This application is a continuation of U.S. patent application Ser. No. 16/965,672, filed on Jul. 29, 2020, which is the National Stage entry of PCT/IB2019/050706, filed on Jan. 29, 2019, which claims priority to India Patent Application Number IN201821003505 filed on Jan. 30, 2018, the entire disclosures of which are hereby incorporated by reference herein.

FIELD OF THE INVENTION

The present invention provides solid state forms of Venetoclax, particularly relates to novel alkali metal salt and/or DMF solvate form of Venetoclax or its salt. The present invention also relates to process for the preparation Venetoclax by using the said solid state form of Venetoclax.

BACKGROUND OF THE INVENTION

Venetoclax is chemically described as 4-(4-{[2-(4-chlorophenyl)-4,4dimethylcyclohex-1-en-1-yl]methyl}piperazin-1-yl)-N-({3-nitro-4-[(tetrahydro-2H-pyran-4ylmethyl)amino]phenyl}sulfonyl)-2-(1H-pyrrolo[2,3-b]pyridin-5-yloxy)benzamide) having the structural Formula (I).

Formula (I)

Venetoclax (VENCLEXTA) is indicated for the treatment of patients with chronic lymphocytic leukemia (CLL) with 17p deletion, as detected by an FDA approved test, who have received at least one prior therapy.

U.S. Pat. No. 8,546,399 (IN 2012DN10067) describes venetoclax exhibit potent binding to a BCL-2 family protein, and pharmaceutically acceptable salts thereof.

U.S. Pat. No. 8,722,657 (IN 2013DN05361) crystalline forms such as pattern A, pattern B, pattern C, pattern D, pattern E, pattern F, pattern G, pattern H, pattern I, pattern J and pattern N of Venetoclax Formula (I).

WO2017/063572 describes crystalline forms such as Form B, Form D, Form F and Form G of Venetoclax.

WO2017/156398 describes crystalline forms such as Form 1, Form 2a, Form 2, Form 3, Form 4, Form 5, Form 6, Form 7, Form 8, Form 9, Form 10, Form 11, Form 12, Form 13, Form 14, and Form 15 of Venetoclax.

Considering the importance of Venetoclax in the pharmaceutical filed, there is a need to develop robust, high yield and commercially viable processes for the preparation of Venetoclax. Accordingly the present invention provides a process for the amorphous form of Venetoclax using alkali metal salt or solvated form of Venetoclax.

SUMMARY OF THE INVENTION

In one aspect, present invention provides alkali metal salt of Venetoclax of Formula (Ia)

Formula (Ia)

wherein, M selected from group comprising of Na, K, Cs, and Li.

In another aspect, present invention provides a process for the purification of Venetoclax comprising the steps of:
i) treating Venetoclax with source of alkali metal in a suitable solvent;
ii) isolating alkali metal salt of Venetoclax;
iii) treating alkali metal salt of Venetoclax with suitable acid; and
iv) isolating Venetoclax.

In yet another aspect, the present invention provides a process for the preparation of the amorphous form of Venetoclax comprising the steps of:
a) obtaining solution of Venetoclax or its salt or its solvate with suitable acid option in presence of suitable solvent;
b) optionally treating the step a) solution with suitable base; and
c) isolating amorphous form of Venetoclax.

DETAILED DESCRIPTION OF THE INVENTION

In an embodiment of the present invention provides alkali metal salt of Venetoclax of Form (Ia)

Formula (Ia)

wherein, M is selected from group comprising of Na, K, Cs and Li.

In another embodiment of the present invention, the alkali metal salt of Venetoclax is Venetoclax sodium, Venetoclax potassium, Venetoclax cesium, Venetoclax lithium preferably Venetoclax sodium. Venetoclax sodium prepared according to the present invention is preferably isolated in the form of solid. The solid form thus obtained may exist in the form of amorphous or crystalline.

In still another embodiment of the present invention, there is provided novel crystalline form of Venetoclax sodium which is designated as Form AL2. Form AL2 of Venetoclax Sodium is characterized by a powder X-ray diffraction pattern comprising 2Θ values (±0.2° 2Θ) selected from the group of 4.47°, 7.88°, 8.92°, 16.36°, 18.53°, 19.21° and 20.71°, ±0.2° 2Θ.

In another embodiment of the present invention, Form AL2 of Venetoclax Sodium is further characterized by a powder X-ray diffraction pattern comprising 2Θ values (±0.2° 2Θ) selected from the group of 3.93°, 6.17°, 6.85°, 9.20°, 10.31°, 12.70°, 14.39°, 14.77°, 15.21°, 15.73°, 16.89°, 17.59°, 17.99°, 20.02°, 21.55°, 22.51°, 23.83°, 24.25°, 24.87°, 25.54°, 27.53°, 28.16°, 29.36°, 30.49°, 33.20°, ±0.2° 2Θ.

Figure 1:
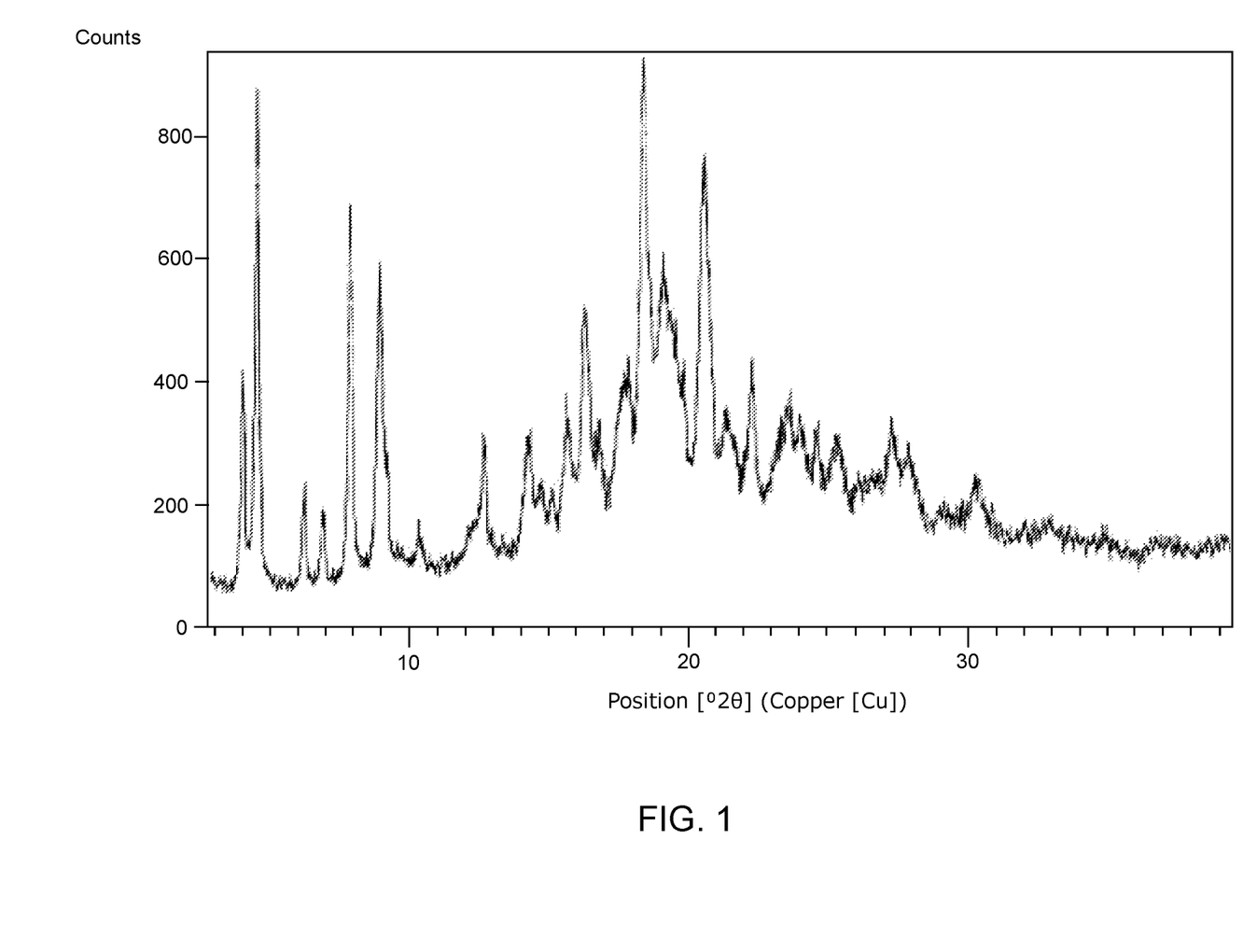
FIG. 1: shows the X-ray powder diffraction pattern of Form AL2 of sodium salt of Venetoclax.

In yet another embodiment of the present invention, Form AL2 of Venetoclax Sodium characterized by a powder X-ray diffraction pattern illustrated by FIG. 1.

In yet another embodiment of the present invention the sodium salt of Venetoclax isolated is having sodium content in the range of 2.50% to about 2.6% with respect to the Venetoclax mono sodium salt. In another embodiment of the present invention the sodium salt may be in solvated form.

In another embodiment of the present invention, there is provided a process for the purification of Venetoclax comprising the steps of:
i) treating Venetoclax with source of alkali metal in a suitable solvent;
ii) isolating alkali metal salt of Venetoclax;
iii) treating alkali metal salt of Venetoclax with suitable acid; and
iv) isolating Venetoclax.

wherein, source of alkali metal is selected from alkali metal hydroxide such as sodium hydroxide, potassium hydroxide, cesium hydroxide and lithium hydroxide; alkali metal carbonate such as sodium carbonate, potassium carbonate, lithium carbonate; alkali metal alkoxide such as sodium methoxide, potassium methoxide, sodium ethoxide, potassium tertiary butoxide or alkali metal bicarbonate such as sodium bicarbonate, potassium bicarbonate, lithium bicarbonate and the like.

In still another embodiment of the present invention Venetoclax is treated with source of alkali metal in suitable solvent at a temperature in the range of 30° C. to 70° C.

In another embodiment of the present invention the Venetoclax used in step (i) is taken directly from the reaction mass or chide Venetoclax, preferably directly from the reaction mass. The content of diamide impurity of formula (II) in crude Venetoclax or Venetoclax obtained from reaction mass is in the range of 0.5% to 10% by HPLC.

In another embodiment of the present invention suitable solvent used in step i) is selected any solvent that does not affect the course of the reaction for example alcoholic solvent such as methanol, ethanol, isopropanol, n-propanol, butanol or polar solvents such as dimethyl formamide, dimethyl sulfoxide, dimethyl acetamide and the like.

In another embodiment of the present invention suitable acid in step (iii) is selected from group consisting of fumaric acid, formic acid, maleic acid, succinic acid, adipic acid, puyrvic acid, malonic acid, glutaric acid, camphoric acid, napthalene sulfonic acid, camphor sulfonic acid, hydrochloric acid, sulphuric acid, Trifluoro acetic acid, citric acid and acetic acid.

In another embodiment of the present invention, the reaction of alkali metal salt of Venetoclax obtained is optionally purified using polar solvent such as dimethyl formamide, dimethyl sulfoxide, dimethyl acetamide and alcoholic solvent like methanol, ethanol and the like. The Venetoclax sodium thus purified may be isolated in solvated form or an anhydrous form.

In another embodiment of the present invention the isolation of alkali metal salt of Venetoclax is carried by methods like addition of suitable anti solvent; cooling the reaction mass; distilling the solvent; evaporation; spray drying; lyophilization; freeze drying or by combination of any of the said method in any order. The isolated alkali metal salt of Venetoclax may be in the form of hydrate, solvate, anhydrous, crystalline or amorphous form. Applicant found the preparation of alkali metal salt of Venetoclax is helpful in removing the impurities particularly diamide impurity of formula (II) and thus the pure Venetoclax is obtained without having tedious downstream process. Thus the alkali metal salt of Venetoclax is converted to Venetoclax by treating with acid and Venetoclax is isolated in the form of solvate, crystalline or amorphous form.

In still another embodiment process for the preparation of Venetoclax sodium salt comprises treating the Venetoclax in alcoholic solvent with sodium ion source selected from sodium hydroxide, sodium bicarbonate, sodium-t-butoxide, sodium carbonate, sodium methoxide at a temperature about 30° C. to 70° C. and cooling the solution below 25° C. to isolate the Venetoclax sodium salt.

In still another embodiment of the present invention, the alkali metal salt of Venetoclax is converted to Venetoclax by treatment with suitable acid which is carried out at a temperature in the range of 30° C. to 80° C.

According to present invention Venetoclax alkali metal salt is isolated, however person skilled in the art can obtain pure Venetoclax without isolation of such salt.

In yet another embodiment, the present invention provides Venetoclax or its alkali metal salt prepared according to the invention is having diamide impurity i.e. compound of Formula (II) less than 0.5%; preferably below 0.3%.

Formula(II)

In yet another embodiment, present invention provides Venetoclax having the compound of Formula (II) less than 0.3% based on a determination by HPLC method.

In yet another embodiment, present invention provides Venetoclax having the compound of Formula (III) less than 0.3% preferably below 0.2%.

Formula (III)

In yet another embodiment, present invention provides a pharmaceutical composition comprising an admixture of a Venetoclax drug substance and a pharmaceutically acceptable carrier, wherein the Venetoclax drug substance comprises compound of Formula (II) less than 0.5% based on a determination by HPLC method.

In an embodiment the present invention, there is provided a process for the preparation of the amorphous form of Venetoclax comprising the steps of:
 a) obtaining solution of Venetoclax or its salt or its solvate with suitable acid optionally in presence of solvent;
 b) optionally treating the step a) solution with suitable base; and
 c) isolating amorphous form of Venetoclax.

In another embodiment of present invention, suitable acid in step a) is selected from group consisting of fumaric acid, formic acid, maleic acid, succinic acid, adipic acid, puyrvic acid, malonic acid, glutaric acid, camphoric acid, naphthalene sulfonic acid, camphor sulfonic acid, citric acid and acetic acid.

In still another embodiment of the present invention, suitable base in step b) is selected from the group consisting of potassium acetate, sodium hydroxide, potassium hydroxide, potassium phosphate, sodium phosphate, sodium bicarbonate, aq. ammonia, ammonium hydroxide and sodium carbonate.

In yet another embodiment of the present invention, solvent in step a) methanol, ethanol, n-propanol, isopropanol, n-butanol, isobutanol, or polar solvent such as dimethyl formamide, dimethyl sulfoxide, dimethyl acetamide or mixtures thereof.

In yet another embodiment of the present invention, treating the solution obtained from step a) optionally with suitable base in the temperature range of 25° C. to 40° C. and isolating amorphous Form of Venetoclax.

The amorphous form obtained by present invention is having moisture content not more than 1.5%, more preferably not more than 1%.

In another embodiment, present invention provides the process for the preparation of Form AL of Venetoclax comprising the steps of:
 i) dissolving Venetoclax or its alkali metal salt in dimethyl formamide;
 ii) adding anti-solvent; and
 iii) isolating Form AL solvate of Venetoclax.

In another embodiment of the present invention, Venetoclax or its alkali metal salt is dissolved in dimethyl formamide at a temperature in the range of 25° C. to 80° C., more preferably 50-60° C. Anti-solvent is added to the solution obtained in step i) at a temperature of about 40-80° C. more preferably at 50-60° C.

In another embodiment of present invention suitable anti-solvent in step ii) is selected from the group comprising of water, alcohols such as methanol, ethanol, n-propanol, isopropanol, n-butanol, isobutanol, or mixtures thereof.

In yet another embodiment, the present invention provides Form AL of Venetoclax characterized by a powder X-ray diffraction pattern comprising 2Θ values (±0.2° 2Θ) selected from the group of 5.97°, 7.48, 13.49°, 15°, 17.66°, 18.17°, 19.63° and 20.23°.

In yet another embodiment, the present invention provides Form AL of Venetoclax further characterized by a powder X-ray diffraction pattern comprising 2Θ values (±0.2° 2Θ) selected from the group of 5.05°, 8.16°, 11.91°, 12.13°, 14.31°, 14.68°, 15.17°, 16.33°, 17.35°, 18.78°, 19.15°, 20.78°, 21°, 21.38°, 21.64°, 22.05°, 22.73°, 23.28°, 23.7°, 24.15°, 24.37°, 24.92°, 25.58°, ±0.2° 2Θ.

In yet another embodiment, the present invention provides Form AL of Venetoclax further characterized by a powder X-ray diffraction pattern comprising 2Θ values (±0.2° 2Θ) selected from the group of 10.11°, 11.17°, 11.47°, 12.38°, 14.68°, 16.84°, 17.14°, 19.88°, 20.78°, 21°, 21.38°, 21.64°, 22.05°, 22.73°, 23.28°, 23.7°, 24.15°, 24.37°, 24.92°, 25.58°, 26.01°, 26.61°, 27.11°, 27.92°, 28.67°, 29.72°, 30.49°, 31.48°, 32.08°, 32.72°, 33.04°, 34.03°±0.2° 2Θ.

Figure 2:
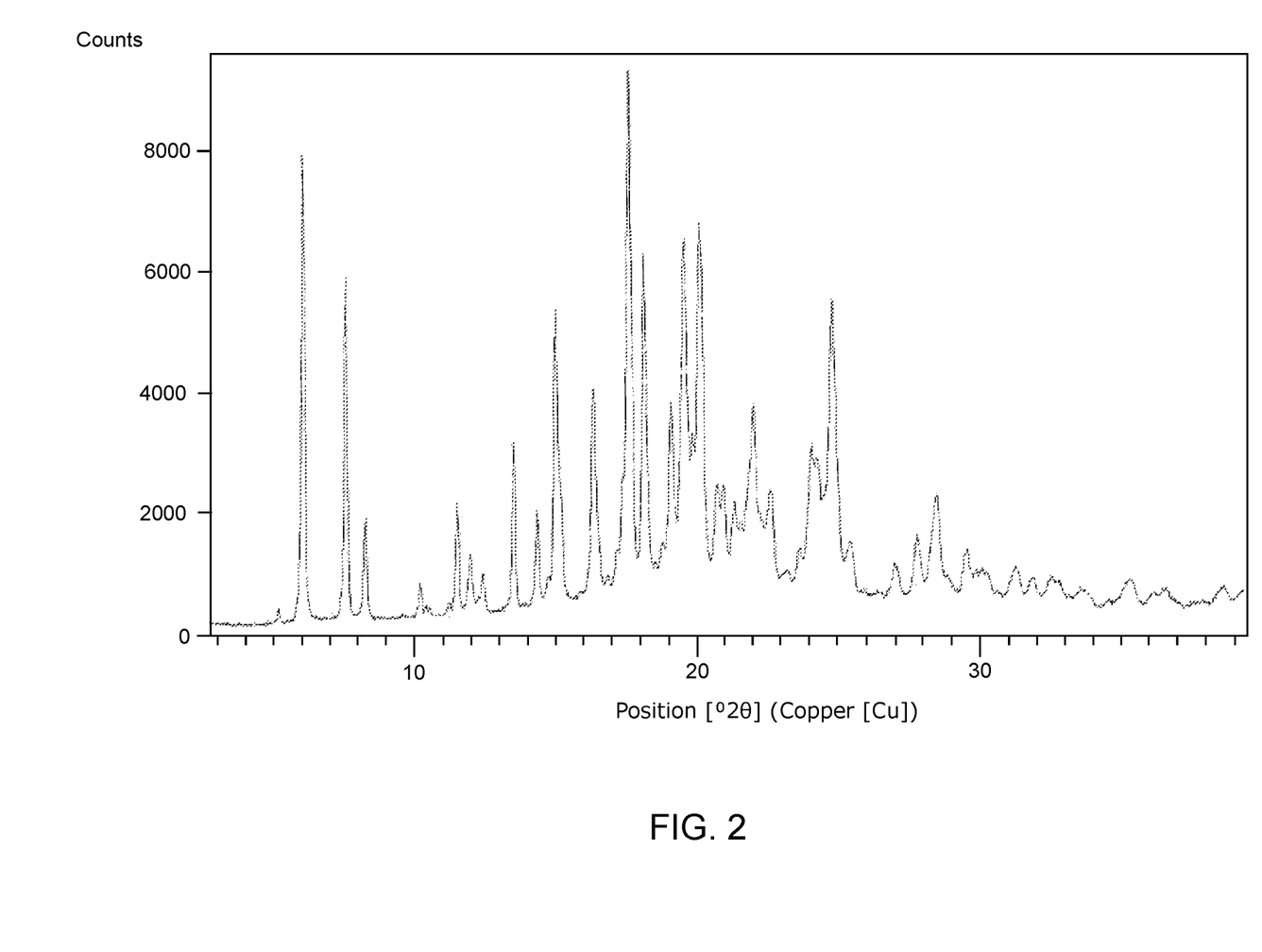
FIG. 2: shows the X-ray powder diffraction pattern of Form AL of Venetoclax.

In yet another embodiment, the present invention provides Form AL of Venetoclax of characterized by a powder X-ray diffraction pattern illustrated by FIG. 2.

Figure 3:
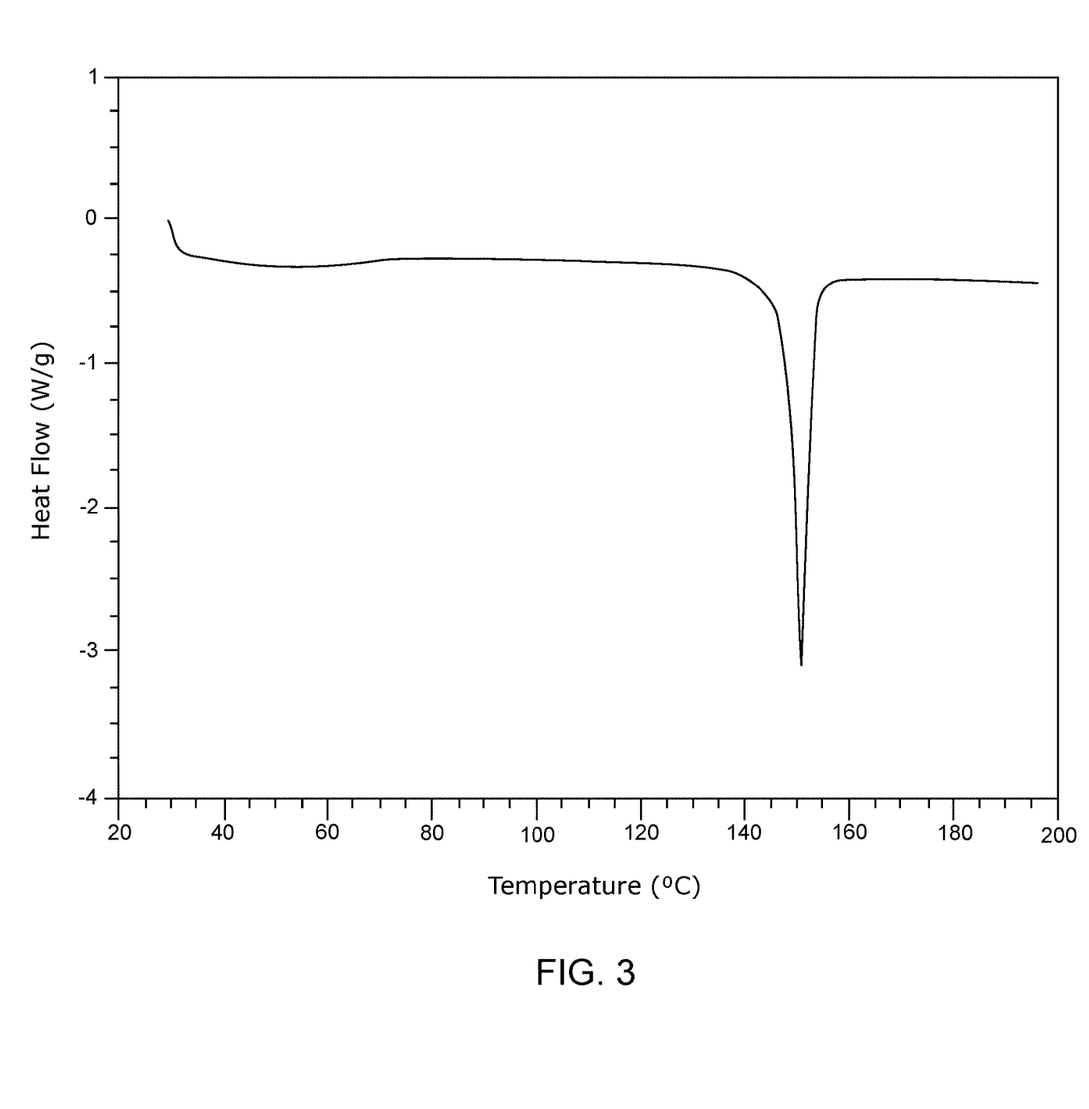
FIG. 3: shows the DSC thermogram of Form AL of Venetoclax.

In yet another embodiment, the present invention provides Form AL of Venetoclax of characterized by a DSC pattern illustrated by FIG. 3.

In yet another embodiment, Form AL may contain dimethyl formamide from about 6.0% to about 10.0%, specifically about 7.75%.

Further, it has been surprisingly found that amorphous form of Venetoclax prepared from alkali metal salt of Venetoclax or its solvate is highly pure and essentially free from any crystalline forms of Venetoclax.

In the foregoing section, embodiments are described by way of an example to illustrate the process of the invention. However, this is not intended in any way to limit the scope of the present invention. Several variants of the example would be evident to persons ordinarily skilled in the art which are within the scope of the present invention.

EXAMPLES

The melting points are measured using Differential Scanning calorimetry (DSC). The equipment is a TA-instruments DSC-Q1000 calibrated at 10 min to give the melting point as onset value. About 2 mg of sample is heated 10 min in a loosely closed pan under nitrogen flow.

X-Ray powder diffractograms were measured on a PANalytical X'Pert PRO X-Ray Diffractometer using CuKa1 radiation. The samples were measured in reflection mode in the 2θ-range 2.5-40° using an X'celerator detector.

1H NMR spectra are recorded at 300 MHz on a Bruker Avance III instrument. Dimethyl sulfoxide (99.8% D) is used as solvent, and tetramethylsilane (TMS) is used as internal reference standard.

For HPLC determination the chromatographic column used was X-Bridge Phenyl (150×4.6) mm, 3.5 μm Detector wavelength: 230 nm Run time: 75 min. and Flow rate: 1.0 ml/min. Buffer preparation: The mobile phase consists of 1.74 g Dipotassium hydrogen phosphate into 1000 ml of water, and sonicated to dissolve. pH at 8.3 was adjusted with dilute orthophosphoric acid. RRT for diamide compound of formula (II) is 1.50.

Example 1: Preparation of Sodium Salt of Venetoclax

To a solution of 2-(1H-pyrrolo[2,3-b]pyridine-5-yloxy)-4-(4-((2-4-chlorophenyl)-4,4-dimethylcyclohex-1-enyl) methyl)piperazin-1-yl)benzoic acid (100 g) in MDC (1500 ml) were added 3-nitro-4-((tetrahydro-2H-1-pyran-4yl) methylamino)benzenesulfonamide (71.78 g), DMAP (6.41 g) and EDCI. HCl (61.16 g) at room temperature and stirred till completion of reaction. After completion of reaction, water was added to the reaction mixture, stirred for 30 minutes and filtered at room temperature. The filtrate was stirred for 30 mins at room temperature and layers were separated. The organic layer (MDC) was distilled atmospherically below at 55° C. to obtain residue (diamide content 5%). To residue methanol (1000 mL) was added and temperature was raised to 50-70° C. and solvent (100 mL) was distilled. To the reaction mass, sodium Hydroxide (10.50 g) solution in methanol was added at 55-60° C. and stirred for 2 hrs. Reaction mixture was cooled to 40-45° C., stirred for 45 mins and filtered. Wet cake was washed with methanol (200 ml). Obtained compound was added to dimethylformamide (300 mL), heated at 50-60° C. and stirred for 30-50 mins to get clear solution. Methanol (300 mL) was added to the solution at 50-60° C. and stirred for 30-50 mins. Reaction mixture was cooled to 25-35° C. and stirred for 8 hrs. The reaction mixture was filtered and solid was washed with mixture of DMF:Methanol (1:3) (100 mL). Wet cake was dried at 25-35° C. for 1 hr in VTD to obtain sodium salt of Venetoclax (Form AL2 of Venetoclax) 80-90 g. (>53% yield) (diamide content >0.3%).

1H NMR (300 MHz, Dimethyl sulfoxide d6) 11.53 (br s, 1H), 8.42 (br s, 1H), 8.34 (t, 1H), 7.95 (d, 1H), 7.64 (t, 2H), 7.27-7.41 (m, 4H), 6.62-6.78 (dd, 2.02), 6.29-6.30 (br s, 2H), 3.83-3.88 (d, 2H), 3.42 (br s, 4H), 3.19-3.29 (m, 6H), 3.01 (br s, 4H), 2.89 (s, 1H), 2.74-2.72 (m, 3H), 2.20 (br s, 6H), 1.95-1.23 (m, 9H), 0.92 (s, 6H).

13C NMR: −170.89, 156.59, 153.06, 149.85, 146.21, 145.00, 142.54, 135.25, 134.99, 134.45, 133.52, 132.57, 131.26, 130.49, 129.66, 129.61, 128.51, 127.37, 125.48, 123.54, 120.02, 116.22, 113.97, 109.76, 106.55, 100.05, 67.13, 60.27, 52.80, 49.09, 48.31, 47.93, 46.78, 36.25, 35.32, 34.34, 31.24, 30.70, 29.33, 28.37.

Example 2: Preparation of Potassium Salt of Venetoclax

To a solution of 2-(1H-Pyrrolo[2,3-b]pyridine-5-yloxy)-4-(4-((2-4-chlorophenyl)-4,4-dimethylcyclohex-1-enyl) methyl)piperazin-1-yl)benzoic acid (100 g) in MDC (1500 ml) were added 3-nitro-4-((tetrahydro-2H-pyran-4yl)methylmaino)benzenesulfonamide (71.78 g), DMAP (6.41 g) and EDCI. HCl (61.16 g) at room temperature and stirred. Water was added to the reaction mixture, stirred for 30 minutes and filtered at room temperature. Obtained filtrate was stirred for 30 mins at room temperature and layers were separated. To aqueous layer, MDC (200 ml) was added at room temperature, stirred for 30 minutes and layers were separated. MDC was distilled atmospherically below 55° C. from the organic layers to obtain residue. Methanol (11000 mL) was added to the residue below 55° C. Temperature was raised to 57-67° C. and solvent (100 mL) was distilled. Potassium Hydroxide (9.67 g) solution in methanol was added to the reaction mass at 55-60° C. and stirred for 2 hrs. Reaction mixture was cooled to 40-45° C., stirred for 45 mins and filtered. Wet cake was washed with (200 ml) methanol. Obtained compound was added to dimethylformamide (300 mL), refluxed at 50-60° C. and stirred for 30-50 mins to obtain clear solution. Methanol (300 mL) was added to the solution and stirred for 30-50 mins. Reaction mixture was cooled to 25-35° C. and stirred for 8 hrs. The reaction mixture was filtered and solid was washed with mixture of DMF:Methanol (1:3) (100 mL). Wet cake was dried at 25-35° C. for 1 hr in VTD to obtain potassium salt of Venetoclax. 80-90 g.

1H NMR (300 MHz, Dimethyl sulfoxide d6) 11.52 (hr s, 1H), 8.39 (br s, 1H), 8.33 (t, 1H), 7.94 (m, 1H), 7.59-7.64 (m, 2H), 7.41 (t, 1H), 7.33-7.36 (d, 2.02), 7.25 (d, 1H), 7.06-7.03 (d, 2H), 6.765 (d, 2H), 6.625 (d, 6.29-6.30 (br s, 2H), 3.87-3.83 (d, 2H), 3.36-3.21 (m, 4H) 3.00 (br s, 4H), 2.74 (br s, 2H), 2.20 (br s, 6H), 1.83-1.95 (m, 2H), 1.59-1.63 (d, 2H), 1.36 (t, 2H), 1.18-1.32 (m, 2H), 0.92 (s, 6H)

13C NMR: −170.43, 156.50, 152.99, 149.90, 146.17, 144.99, 142.56, 135.21, 135.17, 134.45, 133.65, 132.52, 131.26, 130.51, 129.63, 128.52, 127.35, 125.61, 123.70, 120.02, 116.16, 113.88, 109.79, 106.63, 100.05, 67.125, 60.271, 52.815, 48.314, 47.957, 46.791, 35.332, 34.327, 30.711, 29.359, 28.388, 25.679

Example 3: Preparation of Cesium Salt of Venetoclax

To a solution of 2-(1H-Pyrrolo[2,3-b]pyridine-5-yloxy)-4-(4-((2-4-chlorophenyl)-4,4-dimethylcyclohex-1-enyl) methyl)piperazin-1-yl)benzoic acid (100 in MDC (1500 ml) were added 3-nitro-4-((tetrahydro-2H-pyran-4yl)methylmaino)benzenesulfonamide (71.78 g), DMAP (6.41 g) and EDCI. HCl (61.16 g) at room temperature and stirred for 5 hrs. Water was added to the reaction mixture, stirred for 30 minutes and filtered at room temperature. Obtained filtrate was stirred for 30 mins at room temperature and layers were separated. To aqueous layer, MDC (200 ml) was added at room temperature, stirred for 30 minutes and layers were separated. MDC was distilled atmospherically below 55° C. from the organic layers to obtain residue. Methanol (1000 mL) was added to the residue below 55° C. Temperature was raised to 57-67° C. and solvent (100 mL) was distilled. Cesium Hydroxide (25.9 g) solution in methanol was added to the reaction mass at 55-60° C. and stirred for 2 hrs. Reaction mixture was cooled to 40-45° C., stirred for 45 mins and filtered. Wet cake was washed with (200 ml) methanol. Obtained compound was added to dimethylformamide (300 mL), refluxed at 50-60° C. and stirred for 30-50 mins to obtain clear solution. Methanol (300 mL) was added to the solution and stirred for 30-50 mins. Reaction mixture was cooled to 25-35° C. and stirred for 8 hrs. The reaction mixture was filtered and solid was washed with mixture of DMF:methanol (1:3) (100 mL). Wet cake was dried at 25-35° C. for 1 hr in VTD to obtain cesium salt of Venetoclax. 70 g.

Example 4: Preparation of Lithium Salt of Venetoclax

To a solution of 2-(1H-Pyrrolo[2,3-b]pyridine-5-yloxy)-4-(4-((2-4-chlorophenyl)-4,4-dimethylcyclohex-1-enyl) methyl)piperazin-1-yl)benzoic acid (100 g) in MDC (1500 ml) were added 3-nitro-4-((tetrahydro-2H-pyran-4 yl)methylmaino)benzenesulfonamide (71.78 g), DMAP (6.41 g) and EDCI. HCl (61.16 g) at room temperature and stirred for 5 hrs. Water was added to the reaction mixture, stirred for 30 minutes and filtered at room temperature. Obtained filtrate was stirred for 30 mins at room temperature and layers were separated. To aqueous layer, MDC (200 ml) was added at room temperature, stirred for 30 minutes and layers were separated. MDC was distilled atmospherically below 55° C. from the organic layers to obtain residue. Methanol (1000 mL) was added to the residue below 55° C. Temperature was raised to 57-67° C. and solvent (1.00 mL) was distilled. Lithium Hydroxide (4.13 g) solution in methanol was added to the reaction mass at 55-60° C. and stirred for 2 hrs. Reaction mixture was cooled to 40-45° C., stirred for 45 mins and filtered. Wet cake was washed with (200 ml) methanol. Obtained compound was added to dimethylformamide (300 mL), refluxed at 50-60° C. and stirred for 30-50 mins to obtain clear solution. Methanol (300 mL) was added to the solution and stirred for 30-50 mins. Reaction mixture was cooled to 25-35° C. and stirred for 8 hrs. The reaction mixture was filtered and solid was washed with mixture of DMF:methanol (1:3) (100 mL). Wet cake was dried at 25-35° C. for 1 hr in VTD to obtain lithium salt of Venetoclax. 70 g.

Example 5: Preparation of Amorphous Form of Venetoclax

To a solution of Formic acid (150 mL), Venetoclax (100 g) was added at room temperature. Reaction mixture was heated at 40-45° C. to get clear solution. The reaction mixture was filtered at hot condition to remove undissolved particle. To the obtained filtrate aqueous solution of ammonia (560 mL) was slowly added at room temperature. Reaction mixture was cooled to 10-20° C. and pH maintained at 8. The reaction mixture was stirred for 90 mins at room temperature and solid was filtered. The obtained solid was washed with water and dried at room temperature to obtain Amorphous Font of Venetoclax. (>90% yield).

Example 6: Preparation of Amorphous Form of Venetoclax

To a solution of formic acid (150 mL), Venetoclax Sodium (100 g) was added at room temperature. Reaction mixture was heated at 40-45° C. to get clear solution. The reaction mixture was filtered at hot condition to remove undissolved particle. To the obtained filtrate aqueous solution of ammonia (560 mL) was slowly added at room temperature. Reaction mixture was cooled to 10-20° C. and pH maintained at 8. The reaction mixture was stirred for 90 mins at room temperature and solid was filtered. The obtained solid was washed with water and dried at room temperature to obtain Amorphous Form of Venetoclax. (>90% yield).

Example 7: Preparation of Amorphous Form of Venetoclax

To a solution of formic acid (200 mL), Venetoclax (100 g) was added at room temperature. The reaction mixture was heated at 45-50° C. The reaction mixture was filtered at hot condition to remove undissolved particle and washed with formic acid (50 mL). 20% aqueous Potassium phosphate (1060 mL) was slowly added to the filtrate and stirred for 90 mins at room temperature. The obtained solid was filtered, washed with water (100 mL) and dried at room temperature for 1-2 hrs in VTD to obtain amorphous Form of Venetoclax. 90-95 g. (>90% yield).

Example 8: Preparation of Venetoclax DMF Solvate

To a solution of dimethylformamide (300 mL), Venetoclax (100 g) was added at room temperature. The reaction mixture was heated at 50-70° C. and stirred for 30 min. MeOH (300 mL) was added slowly to the reaction mixture at 50-70° C., and stirred for 30 min. The reaction mixture was cooled to 25-40° C. and solid was filtered. The obtained solid was washed with mixture of DMF:Methanol (1:3) (100 mL) and wet cake was dried at 25-35° C. for 1 hr in VTD to obtain Venetoclax DMF solvate (90 g).

Example 9: Preparation of Amorphous Form of Venetoclax

To a solution of formic acid (150 mL), Venetoclax sodium (100 g) was added at room temperature. The reaction mixture was heated at 45-50° C. The reaction mixture was filtered at hot condition to remove undissolved particle and washed with formic acid (50 mL). 20% aqueous Potassium phosphate (1060 mL) was slowly added to the filtrate and stirred for 90 mins at room temperature. The obtained solid was filtered, washed with water (100 and dried at room temperature for 1-2 hrs in VTD to obtain amorphous Form of Venetoclax. 90-95 g. (>90% yield).

Example 10: Preparation of Amorphous Form of Venetoclax

To a solution of formic acid (200 mL), Venetoclax (100 g) was added at room temperature. Reaction mixture was heated at 60-65° C. to get clear solution. The reaction mixture was filtered at hot condition to remove undissolved particle. To the obtained filtrate 20% aqueous solution of potassium carbonate (5480 mL) was slowly added at room temperature and stirred for 4-6 hours. The obtained product was filtered, washed with water and dried to obtain amorphous Form of Venetoclax (>90% yield).

Example 11: Preparation of Amorphous Form of Venetoclax

To a solution of formic acid (200 mL), Venetoclax (100 g) was added at room temperature. The reaction mixture was heated at 60-65° C. The reaction mixture was filtered at hot condition to remove undissolved particle. To the obtained filtrate 20% aqueous NaOH solution (5480 mL) was added at 25-35° C. and stirred for 4-6 hours. The obtained product was filtered, washed with water and dried to obtain amorphous Form of Venetoclax. (>90% yield).

Example 12: Preparation of Amorphous Form of Venetoclax

To a solution of formic acid (200 mL), Venetoclax sodium (100 g) was added at room temperature. The reaction mixture was heated at 60-65° C. The reaction mixture was filtered at hot condition to remove undissolved particle. To the obtained filtrate 20% aqueous NaOH solution (5480 mL) was added at 25-35° C. and stirred for 4-6 hours. The obtained product was filtered, washed with water and dried to obtain amorphous Form of Venetoclax. (>90% yield).

Example 13: Preparation of Amorphous Form or Venetoclax

To a solution of formic acid (200 mL), Venetoclax sodium (100 g) was added at room temperature. Reaction mixture was heated at 65-70° C. to get clear solution. The reaction mixture was filtered to remove undissolved particle. To the obtained filtrate, DM water (1000 mL) was added and stirred for 4-5 hours at 25-35° C. The obtained solid was filtered and given slurry wash with 10% aqueous solution of potassium carbonate (1 L) and water (500 mL). The obtained product was dried to obtain amorphous Form of Venetoclax (85 gm).

Example 14: Preparation of Amorphous Form of Venetoclax

To a solution of formic acid (200 Venetoclax sodium (100 g) was added at room temperature. Reaction mixture was heated at 60-65° C. to get clear solution. The reaction mixture was filtered at hot condition to remove undissolved particle. To the obtained filtrate 20% aqueous solution of potassium carbonate (5480 mL) was slowly added at room temperature and stirred. The obtained product was filtered, washed with water and dried to obtain amorphous Form of Venetoclax. (>90% yield).

Example 15: Preparation of Amorphous form of Venetoclax

To aq. solution of Citric acid (2000 mL), Venetoclax sodium (100 g) in DMF (350 mL) was added at room temperature. Stir the reaction mixture for 1-2 hrs. The obtained solid was filtered and wet product is treated with water, filtered and dried to obtain amorphous Form of Venetoclax. (>90% yield).

Example 16: Preparation of Amorphous Form of Venetoclax

To aq. solution of Citric acid (2000 mL), Venetoclax sodium (100 g) in DMSO (350 mL) was added at room temperature. Stir the reaction mixture for 1-2 hrs. The obtained solid was filtered and wet product is treated with water, filtered and dried to obtain amorphous Form of Venetoclax. (>90% yield).

What is claimed is:

1. Form AL2 of Venetoclax Sodium characterized by the powder X-ray diffraction pattern shown in FIG. 1.

2. A process for the preparation of Form AL2 of Venetoclax Sodium of claim 1, the process comprising:
   treating Venetoclax with a source of sodium ions in a suitable solvent; and
   isolating crystalline Venetoclax Sodium.

3. The process of claim 2, wherein the source of sodium ions is sodium hydroxide and the suitable solvent is methanol.

4. A process for the preparation of Venetoclax, the process comprising:
   treating the Form AL2 of Venetoclax Sodium of claim 1 with a suitable acid, optionally in the presence of a suitable solvent, to form a product;
   optionally treating the product with a suitable base; and
   isolating Venetoclax.

5. The process of claim 4, wherein the suitable acid is selected from the group consisting of fumaric acid, formic acid, maleic acid, succinic acid, adipic acid, pyruvic acid, malonic acid, glutaric acid, camphoric acid, naphthalene sulfonic acid, camphor sulfonic acid, hydrochloric acid, sulphuric acid, trifluoroacetic acid, citric acid and acetic acid.

6. The process of claim 5, wherein the suitable acid is citric acid.

7. The process of claim 4, wherein the suitable base is selected from the group consisting of potassium acetate, sodium hydroxide, potassium hydroxide, potassium phosphate, sodium phosphate, sodium bicarbonate, aqueous ammonia, ammonium hydroxide, and sodium carbonate.

8. The process of claim 4, wherein the suitable solvent is methanol, ethanol, n-propanol, isopropanol, n-butanol, isobutanol, dimethyl formamide, dimethyl sulfoxide, dimethyl acetamide, or mixtures thereof.

9. The process of claim 8, wherein the suitable solvent is dimethyl sulfoxide.

10. The process of claim 4, wherein the suitable acid is citric acid and the suitable solvent is dimethyl sulfoxide.

Figure 4:
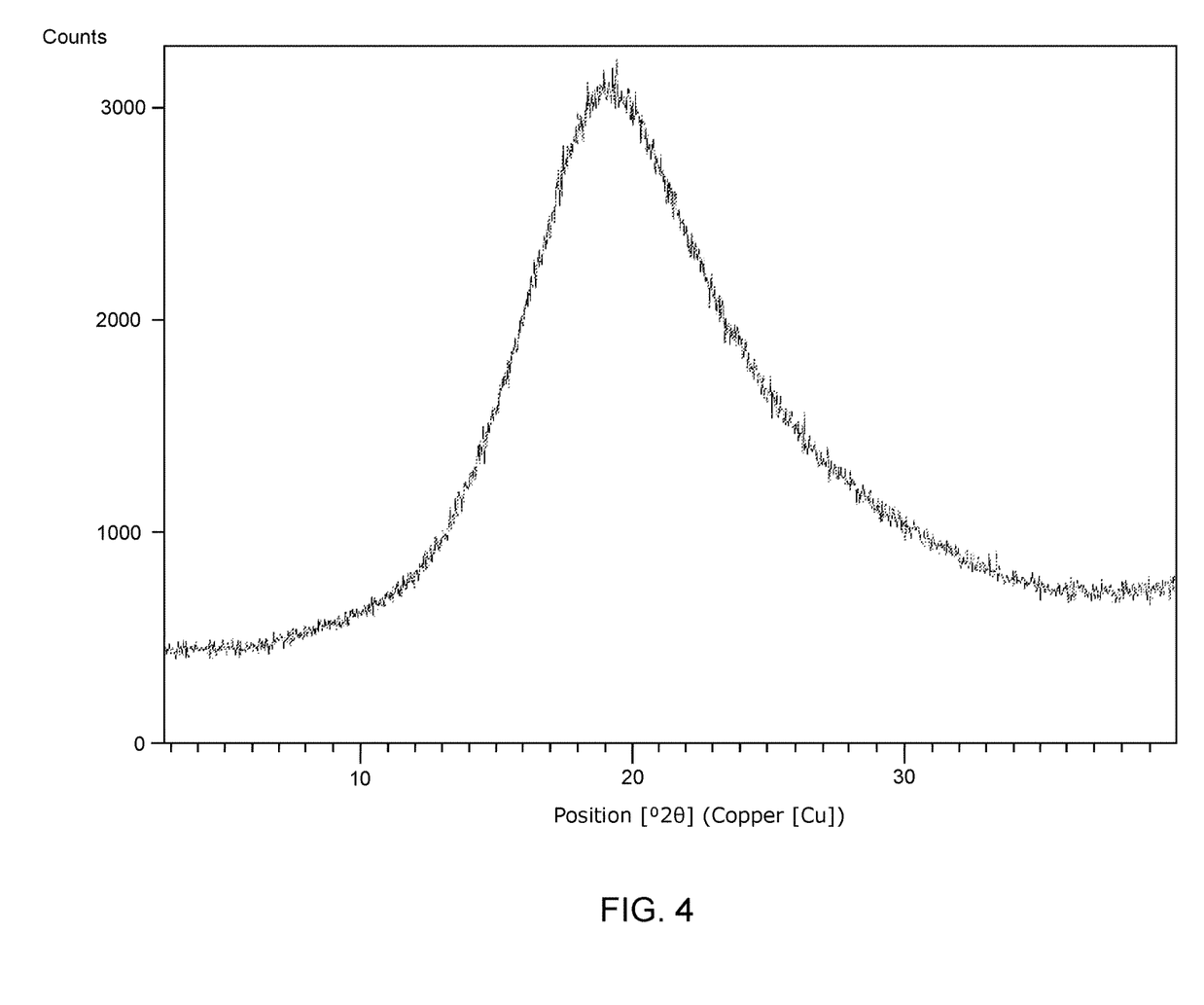
FIG. 4: shows the X-ray powder diffraction pattern of Amorphous Form of Venetoclax.

11. The process of claim 4, wherein the Venetoclax is the amorphous form of Venetoclax characterized by the X-ray diffraction pattern shown in FIG. 4.

12. The process of claim 11, wherein the amorphous form of Venetoclax is free from any crystalline forms of Venetoclax.

13. The process of claim 11, further comprising admixing the amorphous form of Venetoclax and a pharmaceutically acceptable carrier to form a pharmaceutical composition.

14. A process for the preparation of the amorphous form of Venetoclax characterized by the X-ray diffraction pattern shown in FIG. 4, the process comprising:
   treating Venetoclax Sodium with citric acid in the presence of dimethyl sulfoxide; and
   isolating the amorphous form of Venetoclax characterized by the X-ray diffraction pattern shown in FIG. 4.

15. The process of claim 14, wherein the citric acid is in aqueous solution.

16. The process of claim 14, wherein the Venetoclax Sodium is crystalline.

17. The process of claim 14, wherein the amorphous form of Venetoclax is free from any crystalline forms of Venetoclax.

18. The process of claim 14, further comprising admixing the amorphous form of Venetoclax and a pharmaceutically acceptable carrier to form a pharmaceutical composition.

* * * * *